United States Patent [19]

Bezoari

[11] Patent Number: 4,727,175

[45] Date of Patent: Feb. 23, 1988

[54] HYDROXYPHENOXYPHOSPHAZENES AND A PROCESS FOR PRODUCING SAME

[75] Inventor: Massimo D. Bezoari, Baton Rouge, La.

[73] Assignee: The Dow Chemical Company, Midland, Mich.

[21] Appl. No.: 912,464

[22] Filed: Sep. 29, 1986

[51] Int. Cl.$^4$ .............................................. C07F 9/24
[52] U.S. Cl. ...................................................... 558/80
[58] Field of Search ............................................ 558/80

[56] References Cited

U.S. PATENT DOCUMENTS

| | | | |
|---|---|---|---|
| 3,206,494 | 9/1965 | Lund et al. | 558/80 |
| 3,240,728 | 3/1966 | Lund | 260/2.5 |
| 3,446,876 | 5/1969 | Breslow | 260/927 |
| 3,462,518 | 8/1969 | Kober et al. | 260/927 |
| 4,029,634 | 6/1977 | Meredith | 260/45.9 NP |
| 4,107,108 | 8/1978 | Dieck et al. | 521/85 |
| 4,117,041 | 9/1978 | Guechl | 260/927 N |
| 4,124,557 | 11/1978 | Dieck et al. | 260/30.6 R |
| 4,179,555 | 12/1979 | Cheng et al. | 528/168 |
| 4,601,843 | 7/1986 | Carr et al. | 558/80 |

OTHER PUBLICATIONS

Kajiwara et al, "Phosphonitrilic Chloride: 23. Substitution Reaction of Phosphonitrilic Chloride Trimer with Sodium Hydroxymethylphenolate and Polymerization of Substitution Products", Polymer, 1975, vol. 16, Jan., 21–24.

*Primary Examiner*—Anton H. Sutto
*Attorney, Agent, or Firm*—E. E. Spielman; D. R. Howard

[57] ABSTRACT

This invention relates to $R_1$, $R_2$-hydroxyphenoxycyclotriphosphazenes and to a process for their preparation. $R_1$ is a phenoxy-, halophenoxy- or an isopropoxy- group while $R_2$ is a hydroxyphenoxy- or a bis-phenoxy A group. The process comprises reacting $R_1$-chlorocyclotriphosphazene with an $R_2$ salt. The reaction takes place in the presence of an inert organic solvent and at a temperature within the range of from about 20° C. to about 150° C.

22 Claims, No Drawings

HYDROXYPHENOXYPHOSPHAZENES AND A PROCESS FOR PRODUCING SAME

BACKGROUND OF THE INVENTION

This invention relates to isopropoxy- and phenoxyhydroxyphenoxycyclotriphosphazenes and to a process for producing same.

Hydroxyphenoxycyclotriphosphazenes, e.g., triphenoxytris(hydroxyphenoxy)phosphazene, are useful additives in polystyrene blends. These hydroxyphenoxy functionalized cyclotriphosphazenes provide flame retardancy characteristics for the blends without the degree of concomitant polymer degradation experienced when conventional flame retardants, such as monochloropentabromocyclohexane (isomer mixture) and hexabromocyclododecane are used.

It is therefore an object of this invention to provide, as new compositions of matter, isopropoxy- and phenoxyhydroxyphenoxycyclotriphosphazenes. It is also an object of this invention to provide a process for producing such hydroxyphenoxy functionalized cyclotriphosphazenes.

THE INVENTION

This invention relates to isopropoxy- and phenoxyhydroxyphenoxycyclotriphosphazenes of the formula:

$$N_3P_3(R_1)_n(R_2)_{6-n}$$

wherein $R_1$ is an isopropoxy radical of the formula,

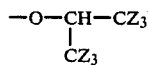

or an aryloxy radical of the formula,

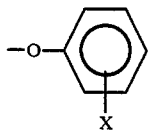

wherein each Z constituent is independently selected for each isopropoxy radical from F and H, wherein each X is independently selected for each aryloxy radical from Cl, Br, F and H, wherein n is a whole integer which is $\geq 1$ and $\leq 5$, and wherein $R_2$ is

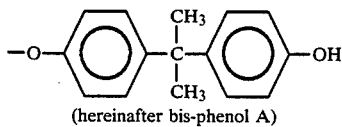

(hereinafter bis-phenol A)

or is a hydroxyphenoxy radical of the formula:

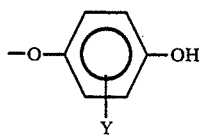

in which each Y is independently selected for each hydroxyphenoxy radical from Cl, Br, F and H. Since Z and X are each independently selected for, respectively, each isopropoxy and aryloxy radical substituent, $R_1$ can represent different radicals in combination. For example, when $R_1$ is an aryloxy, $R_1$ can represent the combination of diphenoxy-(4-bromophenoxy)-(3-chlorophenoxy). See Example 2. Similarly, if $R_1$ is an isopropoxy radical, $R_1$ can represent the combination diisopropoxy-(1,3-difluoroisopropoxy). Further, since Y is independently selected for each hydroxyphenoxy radical, $R_2$ can also represent the combination (3-chloro-3-hydroxyphenoxy)-di(hydroxyphenoxy).

The process of this invention comprises reacting an $R_1$-chlorocyclotriphosphazene having n $R_1$ substituents and $(6-n)$ chloride constituents with an $R_2$ salt for a time period sufficient to yield the desired $R_1$- $R_2$-cyclotriphosphazene. The reaction occurs in the presence of an inert, organic solvent medium and at a temperature within the range of from about 20°C. to about 150° C. The molar ratio of the $R_1$-chlorocyclotriphosphazene reactant to the $R_2$ anion component of the $R_2$ salt is 1:b, wherein b is $>5-n$. Improved yields—indeed, yields of 85% and greater—can be achieved if $b \geq 6-n$.

The subject process may be represented by:

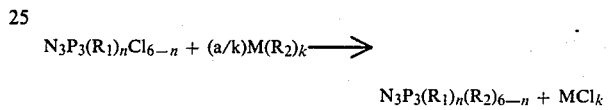

wherein: $R_1$ and $R_2$ are as previously defined; a is greater than $5-n$; M is an inorganic cation, preferably a metal such as Na, K, Li, Ca, Mg and the like; and k is the oxidation state of M and is 1 or 2. As can be seen, the identity of the particular $R_1$- $R_2$-cyclotriphosphazene is dependent upon the respective identities, ring locations and values, as the case may be, for $R_1$, $R_2$ and n found in the two reactants. For example, if triphenoxy-tris(hydroxyphenoxy)cyclotriphosphazene is the desired product, then the reactants, triphenoxy-trichlorocyclophosphazene and a salt of hydroxyphenoxide are used. Further, if the desired product is mono(1,1,1,3,3,3-hexafluoroisopropoxy)-penta(m-chloro-p-hydroxyphenoxy)cyclotriphosphazene, then the reactants are mono(1,1,1,3,3,3-hexafluoroisopropoxy)-pentachlorocyclotriphosphazene and a salt of m-chloro-p-hydroxyphenoxide. If triphenoxy-tris(bis-phenoxy-A)cyclotriphosphazene is the product to be produced, then the reactants are triphenoxytrichlorocyclotriphosphazene and a salt of bisphenol-A.

The $R_2$ substituents are the basic functional groups of the compounds of the invention while the $R_1$ substituents are either inert or functional groups. For example, the $R_1$ substituents are basically inert if they are isopropoxy or phenoxy. Functional $R_1$ groups, such as those contributing to flame retardancy, are exemplified by halophenoxy groups. Fluoro-containing groups are known to provide other characteristics such as thermal stability, and adhesive resistance.

In the process of this invention, the particular inert, organic solvent used is not critical. The solvent need only be inert in the reaction system and be capable of solubilizing the reactants under reaction conditions. For example, solvents such as octane, heptane, hexane, cyclohexane, benzene, toluene, xylene, diglyme, triglyme, tetraglyme, tetrahydrofuran, dioxane and mixtures thereof are all suitable. To achieve convenient temperature control, the process of this invention is preferably run at reflux conditions and, thus, in these preferred cases, the solvent used is one which will provide reflux at the chosen process temperature. A preferred solvent is tetrahydrofuran as it provides good solubility and reflux at a temperature of from about 60° C. to about 70° C.

The subject process is generally run within the temperature range of from about 50° C. to about 140° C. High yields are obtained when the process temperature is within the range of from about 60° C. to about 70° C. Temperatures substantially lower than 50° C., e.g., 0° C., may very well produce the $R_1$-$R_2$-cyclotriphosphazene product sought; however, the yield is predicted to be low and reaction times long. Temperatures much in excess of 140° C. are not desirable as it is expected that some inter- and intra-molecular cross-linking will occur. Such cross-linking lowers the yield of the product. When temperatures above 70° C. are used, it is preferred that the process be initiated at a lower temperature, say about 20° C. to about 50° C., followed by the raising of the temperature up to the selected level. By providing such a temperature profile over process time, the formation, during the initial phase of the process, of undesirable cross-linked products is avoided.

The reaction time for the process of this invention should be sufficiently long to achieve the desired $R_2$ substitution of the chloride constituents initially present in the $R_1$-chlorocyclotriphosphazene reactant. The rate of substitution is interrelated with process temperature. After process initiation, the higher the temperature used, the shorter the reaction period will be. Generally speaking, for the temperature range of 50° C. to 140° C., the reaction period will be about 200 hours for the lower end of the range to about 50 hours for the upper end of the range. For the temperature range of 60° C. to 70° C., the reaction period will be within the range of from about 170 hours to about 70 hours.

While the subject process is preferably run under reflux conditions, it is to be understood, that reflux conditions need not be used, but instead, can be replaced by other temperature control techniques, such as by reactor immersion in a controlled temperature bath.

The order of addition of the $R_1$-chlorocyclotriphosphazene and the $R_2$ salt reactants is not critical. However, agitation, e.g., stirring, is useful in ensuring uniformity of reactant concentrations in the reaction mix.

The determination of a minimum molar ratio of the $R_1$-chlorocyclotriphosphazene to the $R_2$ anion component of the $R_2$ salt is dependent upon the chloride content of the former. As there are 6−n chlorides in each molecule of the phosphazene reactant, the minimum molar ratio of phosphazene reactant to $R_2$ anion which is needed to give some yield of the $R_1$, $R_2$-cyclotriphosphazene product is 1:b where b>5−n. Since reaction yield is determinative of process efficiency, a value of b≧6−n is preferred as such ratio provides the minimum amount of $R_2$ anions needed to replace all of the chlorides in the phosphazene reactant. Generally, a slight molar excess, say, 1 mole percent to about 10 mole percent, of $R_2$ anion will be used to ensure complete chloride substitution. Molar ratios in which 6−n>b>z5−n can be used to produce mixes of partially chloride substituted and completely chloride substituted $R_1$-$R_2$-cyclotriphosphazene product. Such mixes may provide the property sought and thus, in these cases, further chloride substitution may not represent a correct economical choice.

The $R_1$-chlorocyclotriphosphazene reactant has the formula:

$$N_3P_3(R_1)_nCl_{6-n}$$

wherein $R_1$ and n are defined as above.

Exemplary of such reactants are: isopropoxy-pentachlorocyclotriphosphazene; tri(1,1,3,3-tetrafluoroisopropoxy)-trichlorocyclotriphosphazene; tri(1,1,1,3,3,3-hexafluoroisopropoxy)-trichlorocyclotriphosphazene; triisopropoxy-trichlorocyclotriphosphazene; tetraisopropoxydichlorocyclotriphosphazene; diphenoxy-tetrachlorocyclotriphosphazene; triphenoxy-trichlorocyclotriphosphazene; tetraphenoxy-dichlorocyclotriphosphazene; pentaphenoxymonochlorocyclotriphosphazene; tri(o-chlorophenoxy)trichlorocyclotriphosphazene; tetra(p-chlorophenoxy)dichlorocyclotriphosphazene; penta(m-bromophenoxy)monochlorocyclotriphosphazene; di(p-fluorophenoxy)tetrachlorocyclotriphosphazene; and the like.

The $R_1$-chlorocyclotriphosphazene reactant can be conveniently prepared in accordance with the following reaction:

$$(NPCl_2)_3 + (n/k)M(R_1)_k \longrightarrow N_3P_3(R_1)_nCl_{6-n} + MCl_k$$

wherein n, k, M and $R_1$ are as defined previously. The reaction occurs at a temperature within the range of from about 0° C. to about 150° C. and in the presence of an inert organic solvent. The $MCl_k$ salt will form a precipitate and can be filtered from the reaction mix. To ensure that the hexachlorocyclotriphosphazene is not subjected to a molar ratio of hexachlorocyclotriphosphazene to the $R_1$ anion component of the $M(R_1)_k$ salt greater than 1:n/k, the $M(R_1)_k$ salt is added slowly to the reaction mix with the reaction mix being continuously agitated, such as by stirring. The reaction is preferably run at reflux conditions so as to conveniently control the reaction temperature. With a reaction temperature above 60° C., the reaction time is about 0.5 hours to about 48 hours.

The $M(R_1)_k$ salt is conveniently prepared by the reaction of $R_1H$ with a base, such as NaH, to yield the salt and hydrogen. The salt can also be purchased commercially. For example, the isopropoxide salt can be purchased from Morton Thiokol (Alfa), Inc.

As previously shown, the $R_2$ salt reactant has the formula:

$$M(R_2)_k$$

wherein M, k and $R_2$ are as previously defined. The $R_2$ salt can be prepared by the reaction, in an inert organic solvent of $R_2H$ and a base, such as NaH. The $R_2H$ reactant is hydroquinone if the phenoxyhydroxy salt is desired or is bis-phenol A if the bis-phenoxy A salt is desired. When $R_2H$ is a halo-substituted hydroquinone, the resultant salt will likely be a mix of m- and o- halophenoxide due to the essentially equal availability of the hydroxyl groups to deprotonation. The reaction mix should be agitated, e.g., stirred, and is preferably run under reflux conditions. The order of addition of the reactants is not critical. The reaction temperature is within the range of from about 0° C. to about 150° C. and the reaction runs for that period of time necessary to give a good yield of the salt. To maximize the yield of this reaction, the solvent chosen should ensure molecular mobility in the reaction mix even after substantial reaction time has passed. It has been observed that, when tetrahydrofuran is the solvent, the viscosity of the reaction mix can increase to the extent that ease of handling and reaction yields are adversely affected. However, a solvent of tetrahydrofuran/toluene (2:1 to 1:2) gives a less viscous reaction mix and thus a higher reaction yield. Toluene can also be used as sole solvent, and does not show any increase in viscosity. The presence of the toluene in the solvent will change the reflux temperature for the $R_1$-chlorocyclotriphosphazene/$R_2$ salt reaction, however, such a change can still give a reaction temperature within the preferred temperature range of 60° C. to about 70° C. It is also possible to separate the $R_2$ salt from most of the solvent mixture and redissolve it in the solvent chosen for use in the $R_1$-chlorocyclotriphosphazene/$R_2$ salt reaction. In this manner high yields of the salt are obtained and the reflux temperature of the $R_1$-chlorocyclotriphosphazene/$R_2$ salt reaction is highly predictable.

Exemplary of suitable $M(R_2)_k$ salts, dependent on the $R_2$ constituent sought in the final product, are: Sodium p-hydroxyphenoxide; calcium p-hydroxyphenoxide; sodium m- and o- chloro-p-hydroxyphenoxide; magnesium m- and o- bromo-p-hydroxyphenoxide; lithium m- and o- fluoro-p-hydroxyphenoxide; potassium m- and o- chloro-p-hydroxyphenoxide, sodium bis-phenoxide A, potassium bis-phenoxide A, and the like. Preferred are the sodium and potassium salts of p-hydroxyphenoxide.

The following examples are submitted for the purpose of further illustrating the nature of the present invention and are not to be construed as a limitation on the scope thereof.

The NMR spectroscopy used in analyzing the reaction products in various of the following Examples was 31P NMR spectroscopy. In general, the instrument, a JEOL 90X FT NMR, was locked onto acetone-d6, and the shift of 85% $H_3PO_4$ set to zero. Some spectra, however, were obtained with the $H_3PO_4$ standard present. Samples were analyzed in THF solution with a coaxial tube containing acetone-d6.

All spectra exhibited AB2 systems, the appearance of which varies, depending on the ratio of coupling constant, J, to chemical shift difference, v, as described in "Applications of Nuclear Magnetic Resonance Spectroscopy in Organic Chemistry," L. J. Jackman, S. Sternhell, Pergamon Press, London, 1969, pp. 130–132; "Organic Spectroscopy—An Introduction," S. F. Dyke, A. J. Floyd, M. Sainsbury, R. S. Theobald, Penguin, England, 1971, pp. 120–122; and "Nuclear Magnetic Resonance," W. W. Paudler, Allyn and Bacon, Boston, 1971, pp. 115–120. The chemical shifts gave good correlation with shifts reported for similar aryloxyphosphazenes in "Phosphorus-Nitrogen Compounds," H. R. Allcock; Acad Press, New York, 1972; and "The Chemistry of Phosphorus," J. Emsley, D. Hall, Harper and Row, London, 1976, p. 82. The foregoing references are incorporated herein by reference as if fully set forth.

EXAMPLE 1

Preparation of Tetraphenoxybis(hydroxyphenoxy)cyclotriphosphazene

Hydroquinone (11 g, 0.1 mole) was dissolved in 400 ml tetrahydrofuran (THF). To the solution was added sodium hydride (2.6 g, 0.11 mole), with stirring under nitrogen. Evolution of hydrogen was slow, and the mixture was heated at about 60° C. over 48 hours. A further 400 ml THF was added to the resultant slurry, which was refluxed for about 3 more hours.

In a separate reaction sodium hydride (5.0 g, 0.21 mole) was added to a solution of phenol (18.8 g, 0.2 mole) in 350 ml THF. The resultant yellow solution was heated at about 60° C. for about 1 hour and then was added dropwise to a refluxing solution of hexachlorocyclotriphosphazene (17.3 g, 0.05 mole) in THF, over a period of 1.5 hours. The mixture was refluxed for 2 hours, then filtered to give 12 g off-white sodium chloride, after washing with about 50 ml THF. The expected amount was 11.6 g for a 100% yield, indicating a slight loss of adsorbed phosphazene intermediate.

The filtrate was added all at once to the stirring slurry of hydroquinone monosodium salt, and the mixture refluxed for 72 hours. During this time, the slurry became much less viscous. The mixture was filtered, giving a pale green solid, which changes color on drying. The weight of solid was about 9 g (expected weight of sodium chloride: 3.4 g).

The filtered solid was then totally dissolved in water to give final volume of 330 ml. A 3.17 ml aliquot of the solution was titrated to a phenolpthalein end-point with 0.27 ml HCl (0.4M). Therefore, by extrapolation, 0.1 millimoles of aryloxide were present in the total precipitate. Thus, 10% of hydroquinone mono-sodium salt was unreacted.

The remaining filtrate was evaporated at reduced pressure to give a viscous amber oil. Addition of chloroform to the oil caused precipitation of a tan solid, suspected to be hydroquinone due to its insolubility in chloroform. This was confirmed by thin layer chromatographic analysis. The weight of unreacted hydroquinone recovered was 3.9 g.

Evaporation of the chloroform solution at reduced pressure gave back the amber oil, which was analyzed by 31P NMR spectroscopy. The major peak was at −8.2 ppm, which is the correct region for diaryloxy-substituted P nuclei in phosphazene cyclic trimers. The apparent singlet is also the expected pattern for the desired compound.

Other peaks in the spectrum were ascribable to a chloride-containing intermediate in the synthesis. Thus, peaks at −8→−4 ppm were due to diaryloxy-substituted phosphorus in the intermediate, and were coupled (AB2 system) to monochloro-monoaryloxyphosphorus resonating at −19→−24 ppm. Integration of peak areas showed that the ratio of desired compound to intermediate was 3:1, i.e., 75% pure.

The infrared spectrum of the desired compound showed the expected absorptions at (wavenumbers): 3200 (O—H), 3080 (Ar—H), 1595 and 1500 (Ar), 1270 (P═N), and 1160 (Ar—O).

EXAMPLE 2

Preparation of Triphenoxytris(hydroxyphenoxy)cyclotriphosphazene

The same procedure as in Example 1 was used, with the following reagents and quantities: hydroquinone, 33 g (0.3 mole); sodium hydride, 7.4 g (0.31 mole); phenol, 27.9 g (0.3 mole); sodium hydride, 7.4 g (0.31 mole); hexachlorocyclotriphosphazene, 34.5 g (0.1 mole). The total volume of THF required was 2200 ml. This volume was allowed to decrease to 1100 ml during the reaction of the hydroquinone salt and the chloroaryloxycyclotriphosphazene, as the slurry became less viscous.

Filtration yielded a solid which was quickly dissolved in water and titrated with dilute HCl. The quantity of HCl required to neutralize the basic aqueous solution was 0.05 moles, indicating that 8% of the total aryloxides added remained unreacted.

Thin-layer chromatographic analysis of the THF solution showed the absence of unreacted hydroquinone, and the presence of two compounds. The solution was dried over magnesium sulfate, filtered, and the solvent evaporated at reduced pressure to give 63 g of an off-white solid (about 85% yield, based on the weight of expected product).

Analysis of the product by 31P NMR confirmed the presence of two compounds. The major peak at −8.21 ppm was ascribed to the desired product, and could be interpreted as either an AB2 or an A3 system. The minor component was a chloride-containing intermediate, as evidenced by signals at −19→−24 ppm. These were coupled (AB2 system) to nuclei resonating at −4→−8 ppm.

Integration of relative peak areas showed that the desired product constituted about 75% of the product mix.

The infrared spectrum of the mix showed the expected absorptions at (wavenumbers): 3180 (O—H), 3050 (Ar—H), 1590 and 1500 (Ar), 1270 (P=N), and 1150 (Ar—O).

EXAMPLE 3

Preparation of Tetraphenoxybis(hydroxyphenoxy)cyclotriphosphazene

The reagents used were: hydroquinone, 22 g (0.2 mole); sodium hydride, 5 g (0.21 mole); phenol, 37.6 g (0.4 mole); sodium hydride, 9.8 g (0.41 mole); hexachlorocyclotriphosphazene, 34.5 g (0.1 mole).

Hydroquinone monosodium salt was prepared by combination of hydroquinone and sodium hydride in a solvent mixture composed of toluene (250 ml) and THF (150 ml). The mixture was heated at reflux for 72 hours under nitrogen purge, during which time more THF was added to maintain the original volume, as the THF tended to distill off under these conditions. Thus, the reflux temperature was 67°–110° C. Filtration of the reaction mixture gave 26.4 g hydroquinone monosodium salt, as an off-white powder (100% yield). Evaporation of the filtrate yielded no solid, confirming that all the hydroquinone was reacted.

The above solvent combination avoided the viscosity problems encountered with the use of THF only as solvent.

The remainder of the procedure was as in Example 1, except that the reaction was terminated by allowing it to cool, followed by addition of (with mixing) 200 ml water. The aqueous layer was separated and titrated with dilute HCl, which showed that 5% of total aryloxides added remained unreacted. Extraction of the neutralized solution with chloroform, followed by thin-layer chromatographic analysis, revealed the presence of hydroquinone, indicating that the unreacted aryloxide was hydroquinone monosodium salt.

No hydroquinone was detected in the product oil by thin-layer chromatography. Analysis by 31P NMR showed the major constituent to be the desired product, with an extremely small amount (less than 10%) of intermediate (incompletely substituted) monochloro compound.

Since the unreacted aryloxide found by titration was the hydroquinone monosodium salt, and NMR analysis showed that incompletely substituted intermediate constituted 10% of the product mix, the yield of desired product was indicated to be at least 85%.

EXAMPLE 4

Preparation of Triphenoxy-tris(hydroxyphenoxy)phosphazene

The same procedure was followed as in Example 3, with reagents and quantities as in Example 2. However, hydroquinone monosodium salt was formed by combination of reagents in a solution of about 350 ml toluene/THF (1:1). Some increase in viscosity was noted over a 72-hour period, but not as much as with THF alone.

Thin-layer chromatographic analysis of the final reaction mixture, after refluxing for 8 days, showed the presence of the desired compound, as well as hydroquinone. The hydroquinone was removed by evaporation of most of the solvent at reduced pressure, followed by mixing of the resulting oil with a mixture of about 1:4 methanol/water in a blender. The solvents were decanted, and the procedure repeated twice more. The solid obtained was filtered and dried, giving about 65 g of product (about 85% yield).

EXAMPLE 5

Preparation of A Polystyrene Blend

5pph of $N_3P_3(OPh)_3(OArOH)_3$ was blended with STYRON 680 (which is polystyrene, manufactured by The Dow Chemical Company), and kneaded in a Brabender mixing bowl at 200° C. and 50 rpm for 30 minutes. The phosphazene blend showed much less reduction in torque, molecular weight of the polymer, and 10% solution viscosity as compared to a blend of STYRON 680 and FR-651P (which is monochloro-pentabromocyclohexane, manufactured by The Dow Chemical Company), or HBCD (which is hexabromocyclododecane, manufactured by Great Lakes Corporation). These results indicated that less polymer degradation occurred with phosphazenes of this invention than with the FR-651P and HBCD.

TGA data on the blend of this invention also showed that initial degradation temperatures were high. For example, isothermal analysis gave 335° C. as 5% weight loss point for the blend, compared to 320° C. for pure polystyrene. Blends with FR-651P or MBCD gave initial degradation temperatures below 320° C. Furthermore, increasing phosphazene content gave increasing thermal stability, whereas increasing FR-651P or HBCD content gave decreasing thermal stability.

I claim:
1. A process for the production of a compound of the formula,

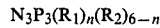

wherein $R_1$ is an isopropoxy radical having the formula

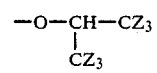

or an aryloxy radical having the formula

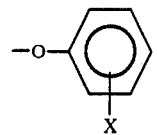

wherein each Z is independently selected for each isopropoxy radical from F and H, each X is independently selected for each aryloxy radical from Cl, Br, F and H, wherein n is a whole integer which is $\geq 1$ and $\leq 5$, and wherein $R_2$ is

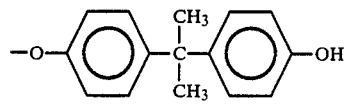

or is a hydroxyphenoxy radical having the formula:

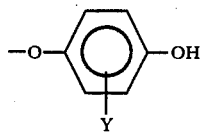

in which Y is selected from Cl, Br, F and H, said process comprising, reacting an $R_1$-chlorocyclotriphosphazene having n $R_1$ substituents and 6-n chloride constituents and an $R_2$ salt for a time period sufficient to yield said compound, said reaction occurring in an inert organic solvent medium, at a temperature within the range of from about 20° C. to about 150° C., and with a molar ratio of said $R_1$-chlorocyclotriphosphazene to the $R_2$ anion component of said $R_2$ salt of 1:b, wherein $b > 5 - n$.

2. The process of claim 1 wherein said $R_2$ salt is an alkali metal salt.

3. The process of claim 1 wherein said $R_2$ salt is a hydroxyphenoxide salt.

4. The process of claim 1 wherein said $R_2$ salt is sodium p-hydroxyphenoxide salt.

5. The process of claim 1 wherein said $R_2$ salt is a bis-phenoxide A salt.

6. The process of claim 1 wherein said $R_2$ salt is sodium bis-phenoxide A.

7. The process of claim 1 wherein said temperature is within the range of from about 50° C. to about 140° C.

8. The process of claim 1 wherein n is 3 or 4.

9. The process of claim 1 wherein $b \geq 6 - n$.

10. The process of claim 1 wherein $R_1$ is said aryloxy radical.

11. The process of claim 1 wherein $R_1$ is said aryloxy radical and all X's are H.

12. The process of claim 11 wherein n is 3 or 4.

13. The process of claim 1 wherein $R_1$ is said isopropoxy radical.

14. The process of claim 1 wherein $R_1$ is said isopropoxy radical and all Z's are H.

15. The process of claim 14 wherein n is 3 or 4.

16. The process of claim 12 wherein $b \geq 6 - n$.

17. The process of claim 15 wherein $b \geq 6 - n$.

18. The process of claim 4 wherein n is 3 or 4, $R_1$ is said aryloxy radical and all X's are H and $b \geq 6 - n$.

19. The process of claim 6 wherein n is 3 or 4, $R_1$ is said aryloxy radical and all X's are H and $b \geq 6 - n$.

20. The process of claim 4 wherein n is 3 or 4, $R_1$ is said isopropoxy radical and all Z's are H and $b \geq 6 - n$.

21. The process of claim 6 wherein n is 3 or 4, $R_1$ is said isopropoxy radical and all Z's are H and $b \geq 6 - n$.

22. Compounds of the formula, $$N_3P_3(R_1)_n(R_2)_{6-n}$$

wherein $R_1$ is an isopropoxy radical having the formula

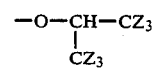

or an aryloxy radical having the formula

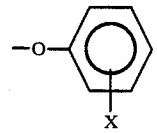

wherein n is a whole integer which is $\geq 1$ and $\leq 5$, each Z is independently selected for each isopropoxy radical from F and H, each X is independently selected for each aryloxy radical from Cl, Br, F and H, and wherein $R_2$ is

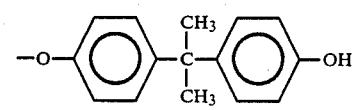

or is a hydroxyphenoxy radical having the formula:

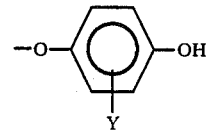

in which each Y is independently selected for each hydroxyphenoxy radical from Cl, Br, F and H.

* * * * *